United States Patent
Perry

(10) Patent No.: US 8,721,577 B1
(45) Date of Patent: May 13, 2014

(54) ANTI-FATIGUE DEVICE

(76) Inventor: Robert J. Perry, Oklahoma City, OK (US)

( * ) Notice: Subject to any disclaimer, the term of this patent is extended or adjusted under 35 U.S.C. 154(b) by 246 days.

(21) Appl. No.: 13/077,628

(22) Filed: Mar. 31, 2011

Related U.S. Application Data

(60) Provisional application No. 61/319,685, filed on Mar. 31, 2010.

(51) Int. Cl.
*A61F 5/00* (2006.01)

(52) U.S. Cl.
USPC .............................. 602/19; 297/284.3; 602/36

(58) Field of Classification Search
USPC .................. 602/19, 36, 40; 297/283.1–283.3, 297/284.1, 284.3, 452.18–452.19, 452.63; 128/846, 869, 874, 875; 2/462; 244/122 R, 122 AG
See application file for complete search history.

(56) References Cited

U.S. PATENT DOCUMENTS

| | | | |
|---|---|---|---|
| 5,022,385 A | 6/1991 | Harza | |
| 5,460,427 A | 10/1995 | Serber | |
| 5,678,891 A * | 10/1997 | O'Neill et al. | ............. 297/284.6 |
| 6,946,183 B2 | 9/2005 | Malpass et al. | |
| 7,663,502 B2 | 2/2010 | Breed | |
| 7,703,152 B2 | 4/2010 | Rhodes et al. | |
| 8,308,670 B2 * | 11/2012 | Sandifer et al. | ................. 602/19 |

* cited by examiner

*Primary Examiner* — Patricia Bianco
*Assistant Examiner* — Camtu Nguyen
(74) *Attorney, Agent, or Firm* — San Diego IP Law Group, LLP

(57) ABSTRACT

An exemplary embodiment of an anti-fatigue device includes a framework worn adjacent a body of a user; and interaction of a cable and the framework provides an anti-gravity support of the body that reduces user fatigue from an activity the user performs. In another exemplary embodiment, the anti-fatigue device includes a head support halo coupled to the framework, the head support halo provides an anti-gravity support of the head that reduces user fatigue while the user performs the activity. In an alternative exemplary embodiment, the anti-fatigue device includes a leg support that substantially secures the framework adjacent the body while the user stands to perform the activity. In yet another exemplary embodiment, the anti-fatigue device includes a seat plate worn adjacent a buttock of the user substantially secures the framework adjacent the body while the user sits on the buttock to perform the activity.

16 Claims, 11 Drawing Sheets

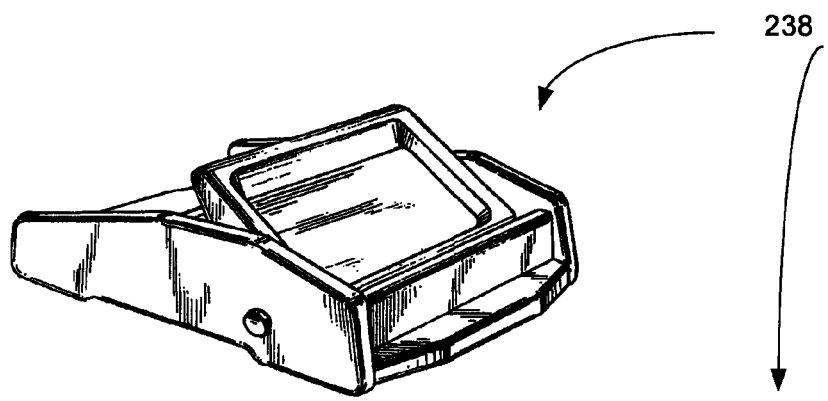
FIG. 11
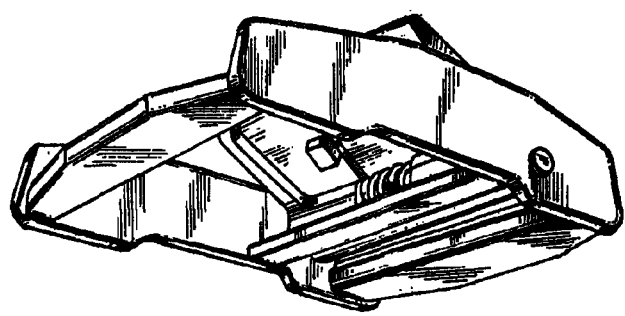
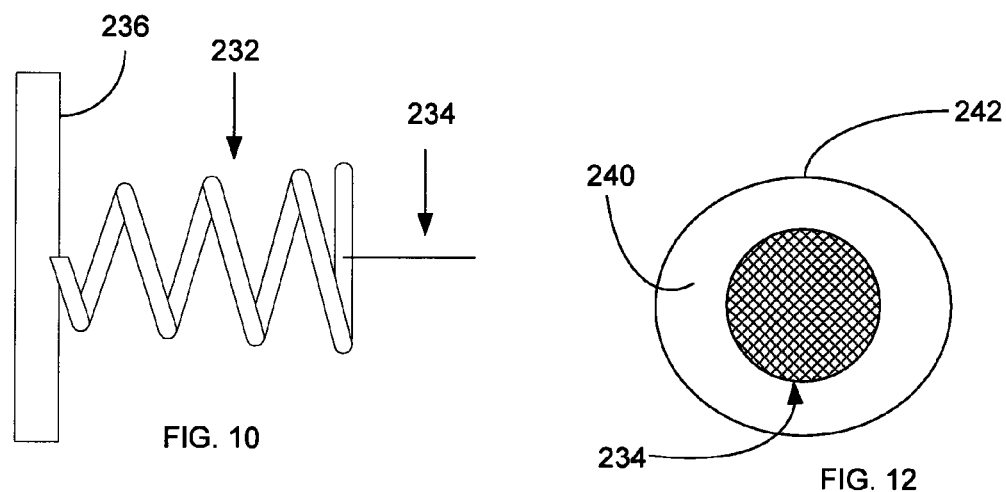
FIG. 10
FIG. 12

ANTI-FATIGUE DEVICE

RELATED APPLICATION

This application claims priority to U.S. Provisional Application No. 61/319,685 filed Mar. 31, 2010, entitled "Anti-Fatigue Device."

FIELD OF THE INVENTION

This invention relates to labor device, and in particular, but not by way of limitation, to labor that functions as an anti-fatigue device for a user performing an activity.

BACKGROUND

A user may perform an activity, e.g., surgery or ceiling repair, that leads to user fatigue, in which for a prolonged time the user assumes a substantially stationary posture. Assuming the substantially stationary posture for the prolonged time may lead to discomfort or trauma in the user (e.g., musculoskeletal system, in particular the spine, shoulder region, and legs) which may be caused by or worsened by fatigue in the user. The user discomfort or trauma may be prevented or relieved by an anti-fatigue device supporting the user in the stationary posture.

Supporting the user performing an activity for a prolonged time may be most effective if the anti-fatigue device is portable, e.g., the user wears the anti-fatigue device. If the user wears the anti-fatigue device, it may be effective to have on/off, or engaged and non-engaged, states so that the user can walk relatively freely when the anti-fatigue device is non-engaged, but the user can engage the anti-fatigue device when needed. Ideally, the anti-fatigue device worn by the user can be used in the standing, sitting, lying, and any other posture that the user needs to assume for performing the activity.

There exists a need in the art for the anti-fatigue device wearable by the user, so that the user can assume a variety of postures, where the anti-fatigue device prevents or relieves discomfort or trauma associated with the posture.

SUMMARY OF THE INVENTION

In accordance with exemplary embodiments, an anti-fatigue device wearable by a user to prevent or relieve discomfort or trauma associated with an assumed posture.

In a first exemplary embodiment, an anti-fatigue device that preferably includes at least a framework is provided. The framework preferably includes at least a first of a plurality of support members interacting with a shoulder hookup member, and a shoulder connection member communicating with a second of the plurality of support members. Preferably the framework is worn adjacent a body of a user. Further communicating with the framework is a preferred shoulder cable, which has a medial portion configured to extend across the body of the user and disposed between opposing first and second ends. Preferably, the first end of the shoulder cable couples to the shoulder hookup member, and the second end couples to the shoulder connection member. In a preferred embodiment, the interaction of the shoulder cable and the framework provides an anti-gravity support of the body of the user.

In a second exemplary embodiment, preferably the framework includes at least a plurality of interconnected backbone plates movable with respect to each other, a backbone hookup member coupled to at least one of the plurality of interconnected backbone plates, and a backbone connection member coupled to at least one of the plurality of interconnected backbone plates, the backbone hookup member and the backbone connection member coupled to each other by a backbone cable therebetween, wherein the user configures the backbone cable to a predetermined length so that the plurality of interconnected backbone plates are substantially immovable with respect to each other in at least a first direction during the anti-gravity support.

In a third exemplary embodiment, preferably the framework includes a shoulder portion that communicates with the shoulder cable, the shoulder portion spreads a support force developed by the anti-gravity support over the body of the user.

In a fourth exemplary embodiment, preferably the framework includes at least a head hookup member, and a head support halo coupled to the head hookup member. Preferably the head support halo includes a head connection member interacting with a head support cable to non-rigidly couple the head hookup member. The head support halo is preferably worn adjacent a head of the user to provide an anti-gravity support of the head, which reduces user fatigue while the user performs the activity.

In a fifth exemplary embodiment, preferably the framework includes at least a leg hookup member, a leg support that includes at least a leg connection member coupled to the leg hookup member by way of a leg support cable. The leg support is preferably worn adjacent a leg of the user, and substantially secures the framework adjacent the body of the user while the user stands on a leg to perform an activity.

In a sixth exemplary embodiment, preferably the framework includes at least a seat portion worn adjacent a buttock of the user, the seat portion substantially secures the framework adjacent the body and the buttock while the user sits on the buttock to perform an activity.

In a seventh exemplary embodiment, preferably the seat portion includes at least a plurality of seat plates movable with respect to each other, a seat hookup member coupled to at least one of the plurality of seat plates, and a seat connection member coupled to at least one of the plurality of seat plates, the seat hookup member and the seat connection member coupled to each other by a seat cable, and wherein the user configures the seat cable to a predetermined length so that the plurality of seat plates are substantially immovable with respect to each other in at least a first direction during the anti-gravity support.

In an eighth exemplary embodiment, a method of providing an anti-gravity support of a body of a user that reduces user fatigue from an activity the user performs is formed by steps comprising: furnishing a backbone portion worn adjacent the body; attaching a shoulder cable to the backbone portion, wherein the shoulder cable captures the body adjacent the backbone portion; attaching a leg cable between the backbone portion and a leg of the user, wherein the wherein the leg cable is configured to substantially secure the backbone portion adjacent the body while the user stands on the leg; and engaging the shoulder cable while the user stands on the leg to provide an anti-gravity support of the body of the user that reduces user fatigue from the activity the user performs.

The ninth exemplary embodiment, the method of providing an anti-gravity support of a body of a user that reduces user fatigue from an activity the user performs is formed by steps comprising: furnishing a backbone portion has shoulder cable, a leg cable, and a head cable, wherein the body is captured by the shoulder cable adjacent the backbone portion worn, the leg cable is coupled to a leg of the user, and the head cable is coupled to a head of the user; engaging the leg cable when the user stands on the leg substantially secures the framework adjacent the body; engaging the shoulder cable when the user leans the body away from a neutral vertical position; and engaging the head cable when the user leans the head away from the neutral vertical position to provide an anti-gravity support of the body of the user that reduces user fatigue from the activity the user performs.

These and various other features and advantages that characterize the claimed invention will be apparent upon reading the following detailed description and upon review of the associated drawings.

BRIEF DESCRIPTION OF THE DRAWINGS

FIG. 10 shows a biasing member disposed in series with the cable.

FIG. 11 illustrates a cam buckle used to join cable segments.

FIG. 12 portrays in section view an exemplary embodiment of the cable may be captured in a lumen of a cableway.

DETAILED DESCRIPTION OF EXEMPLARY EMBODIMENTS

Detailed descriptions of the exemplary embodiments are provided herein. It is to be understood, however, that the present invention may be embodied in various forms. Various aspects of the invention may be inverted, or changed in reference to specific part shape and detail, part location, or part composition. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
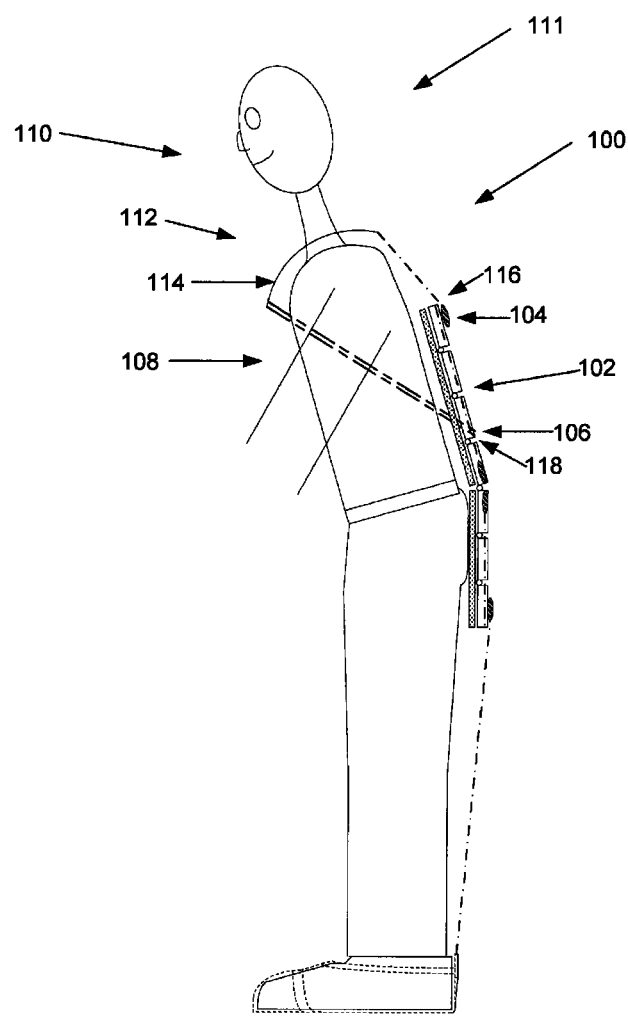
FIG. 1 depicts in side view an exemplary embodiment of an anti-fatigue device.

FIG. 1 shows in side view an exemplary embodiment of an anti-fatigue device 100 includes at least a framework 102 with at least a shoulder hookup member 104 and a shoulder connection member 106 secured thereon, the framework 102 is preferably worn adjacent a body 108 of a user 110. Securing the framework to the user is a shoulder attachment 112 (also referred to herein as a shoulder attachment 112), which has opposing first and second ends (116, 118) and a medial portion 114 disposed there between. The shoulder attachment 112 is preferably configured to extend across the body 108, wherein the first end 116 couples to the shoulder hookup member 104 and the second end 118 couples to the shoulder connection member 106. Interaction of the shoulder attachment 112 and the framework 102 provides an anti-gravity support of the body 108 that reduces user 110 fatigue resulting from an activity performed by user the 110. The anti-fatigue device 100 is engaged when providing the anti-gravity support and disengaged with not providing the anti-gravity support. The user 110 leans away from a neutral vertical position 111 to engage the antigravity device 100.

By providing anti-gravity support to the user 110 who performs an activity that usually requires eccentric contraction of muscles against gravity, the anti-fatigue device 100, reduces user 110 fatigue from the activity. For example, a surgeon, or factory worker, wearing the anti-fatigue device 100 will have reduced fatigue in normally eccentrically contracting muscles, such as the paraspinal, neck, and shoulder muscles, needed to lean forward.

Figure 2:
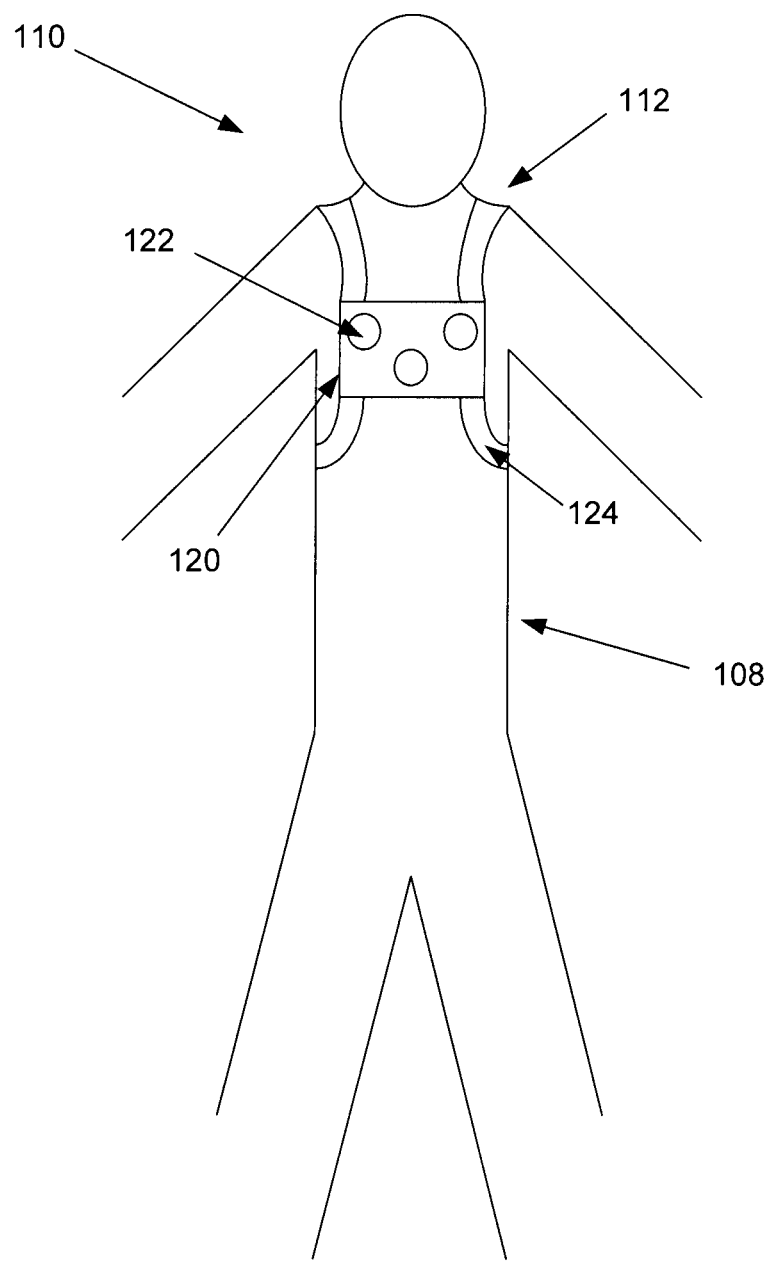
FIG. 2 demonstrates in front view an exemplary embodiment there are at least a pair of shoulder cables and interface controls.

FIG. 2 shows in front view an exemplary embodiment there are at least a pair of shoulder cables 112 to provide a consistent and symmetric fit that facilitates distributing the anti-gravity support forces experienced by the user 110 throughout the body 108. A front portion 120 stabilizes the pair of shoulder cables 112 in a predetermined position relative to each other, and the front portion 120 provides a convenient location for a control interface 122. A lateral portion 124 of the shoulder attachment 112 provides lateral stability that helps secure the framework 102 in a relatively consistent predetermined position to the body 108 while the user 110 performs the activity.

Figure 3:
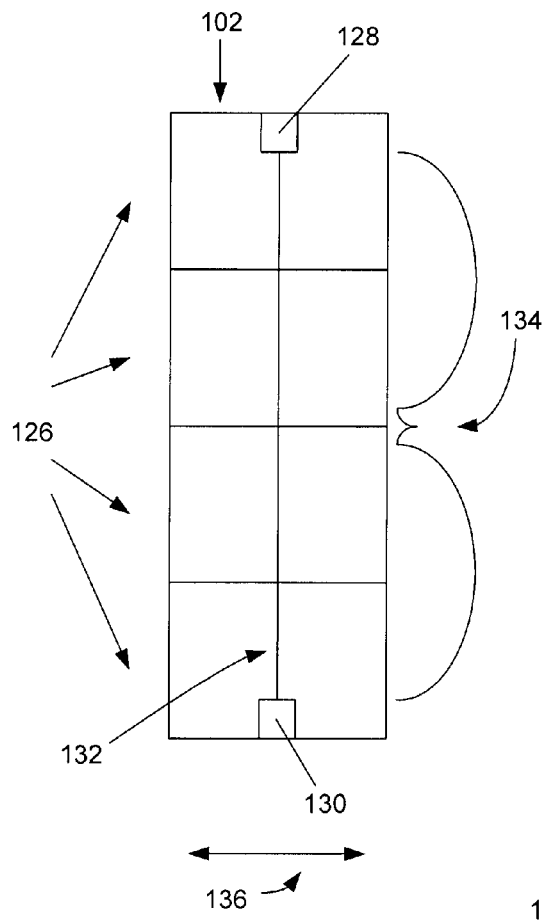
FIG. 3 reveals in section side view an exemplary embodiment of the framework includes at least a plurality of interconnected backbone plates.

FIG. 3 illustrates in section side view an exemplary embodiment of the framework 102 includes at least a plurality of interconnected backbone plates 126 movable with respect to each other, a backbone hookup member 128 coupled to at least one of the plurality of interconnected backbone plates 126, and a backbone connection member 130 coupled to at least one of the plurality of interconnected backbone plates 126, the backbone hookup member 128 and the backbone connection member 130 coupled to each other by a backbone cable 132 therebetween, wherein the user configures the backbone cable 132 to a predetermined backbone cable length 134 so that the plurality of interconnected backbone plates 126 are substantially immovable with respect to each other in at least a first backbone direction 136 during the anti-gravity support.

The plurality of interconnected backbone plates 126 provide flexibility to the framework 102, which allows the framework to provide the user 110 with an optimal fit that is secure to the body 108 and yet comfortable while performing a prolonged activity. Four backbones plates are shown in a preferred embodiment of FIG. 3, but any suitable number may be used. In addition, the skilled artisan will understand that each backbone plate 126 may be of uniform size and shape, or each backbone plate may be of different size and contour as needed.

Figure 4:
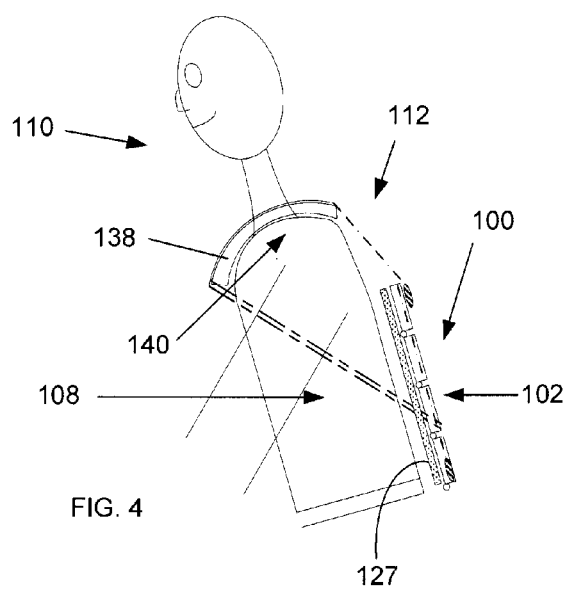
FIG. 4 shows exemplary embodiment of the anti-fatigue device includes at least a shoulder portion.

FIG. 4 portrays exemplary embodiment of the anti-fatigue device 100 includes at least wherein the framework 102 includes a shoulder portion 138 communicates with the shoulder attachment 112, the shoulder portion 138 spreads over the body 108 a support force experienced by the user 110 from the anti-gravity support. Preferably, a shield 127 is interposed between the user 110 and plurality of interconnected backbone plates 126. The shield 127 is provided to aid in the comfort of the framework 102 when worn by the user 110.

By spreading the support force experienced by the user 110 during the anti-gravity support over a larger area than is often practical with the shoulder attachment 112, the user 110 experiences less pressure contacting the body 108 in a given location for the same amount of force applied to the body 108. The user 110 experiences less discomfort from the shoulder attachment 112 digging into the body 108 and the user 110 experiences a more consistent fit over time while wearing the anti-fatigue device 100. In addition, the shoulder attachment 112 operating in conjunction with shoulder portion 138 is less likely to cause abrasions, contusions, swelling, blood clotting, or other untoward effects adjacent the shoulder attachment 112. The shoulder portion 138 is configured to permit substantially unrestricted range of motion at a shoulder 140, so the user 110 can efficiently perform the activity while wearing the anti-fatigue device 100.

Figure 5:
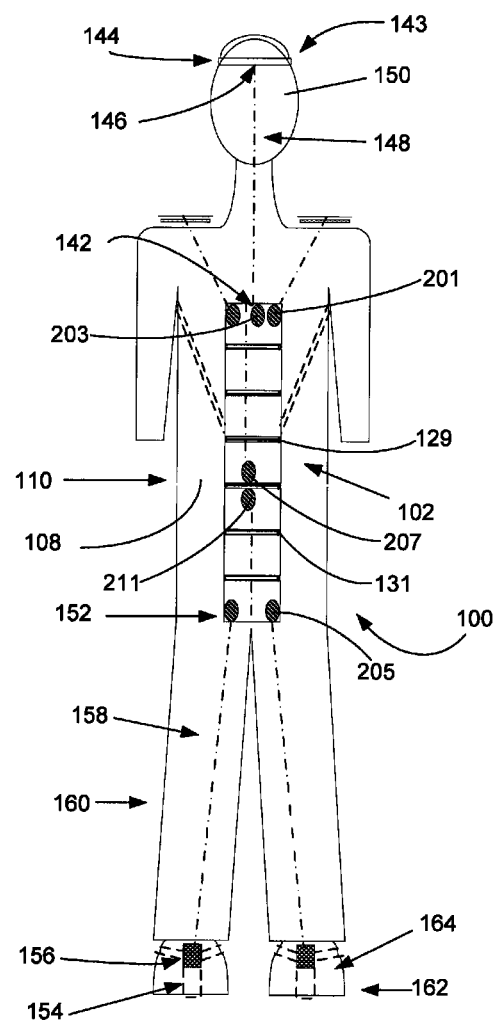
FIG. 5 illustrates in back view an exemplary embodiment of the anti-fatigue device includes at least a head support halo.

FIG. 5 depicts in back view an exemplary embodiment of the anti-fatigue device 100 includes at least wherein the framework 102 includes at least a head hookup member 142, attached to a head support structure 143, which preferably includes at least a head support halo 144 attached to a head connection member 146 that is preferably coupled to the head hookup member 142 using a head support cable 148 (also referred to herein as a head support attachment 148) secured to the head connection member 146 at a first end, and to the framework 102 at a second end. The head support halo 144 is preferably worn adjacent a head 150 of the user 110. In an active mode, the head support structure provides an anti-gravity support of the head 150 of the user 110, while the user 110 performs an activity. Further in a preferred embodiment, the plurality of interconnected backbone plates 126 are interconnected by a backbone attachment 129, while the plurality of interconnected seat plates are interconnected by a seat attachment 131.

An exemplary embodiment of the anti-fatigue device 100 that includes the head support halo 144 provides further reduction in fatigue for the user 110 leaning the head 150 forward, because leaning the head 150 forward normally requires eccentric contraction of muscles to support the head 150. Proving anti-gravity support to a neck or cervical paraspinal muscles (not shown) inherently provides anti-gravity support to the head 150.

FIG. 5 further depicts an exemplary embodiment of the anti-fatigue device 100 includes at least wherein the framework 102 includes at least a leg hookup member 152, a leg support 154 includes at least a leg connection member 156 coupled to the leg hookup member 152 by a linking member 158. The leg support 154 is preferably worn adjacent a leg 160 of the user 110 and substantially secures the framework 102 adjacent the body 108 while the user 110 stands to perform an activity.

When the user 110 performs the activity standing on the leg 160, the leg support 154 is configured to experience tension and to apply tension through the shoulder attachment 112, which helps to substantially secure the framework 102 in a predetermined relative position adjacent the body 108, and facilitate the anti-gravity support.

Figure 6:
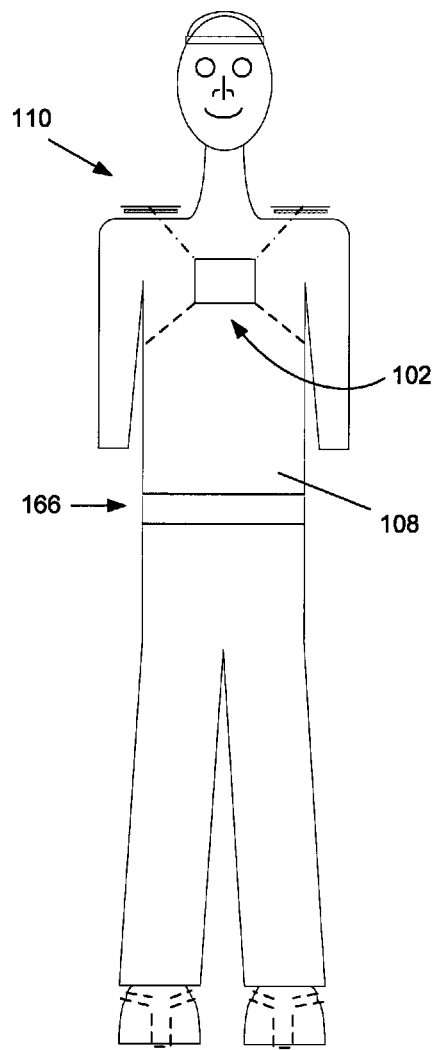
FIG. 6 portrays in front view in another alternative embodiment, the framework has a securing support that surrounds the body.

In an exemplary embodiment, the leg support 154 is contacting a shoe 162 adjacent a foot 164 of the user 110. In another exemplary embodiment, the leg support 154 is integrated into the shoe 162. In an alternative embodiment, the leg support 154 is secured to another leg portion of the user 110. FIG. 6 reveals in front view another alternative embodiment, the framework 102 has a securing support 166 that surrounds the body 108 to substantially secure the framework adjacent the body 108.

Figure 7:
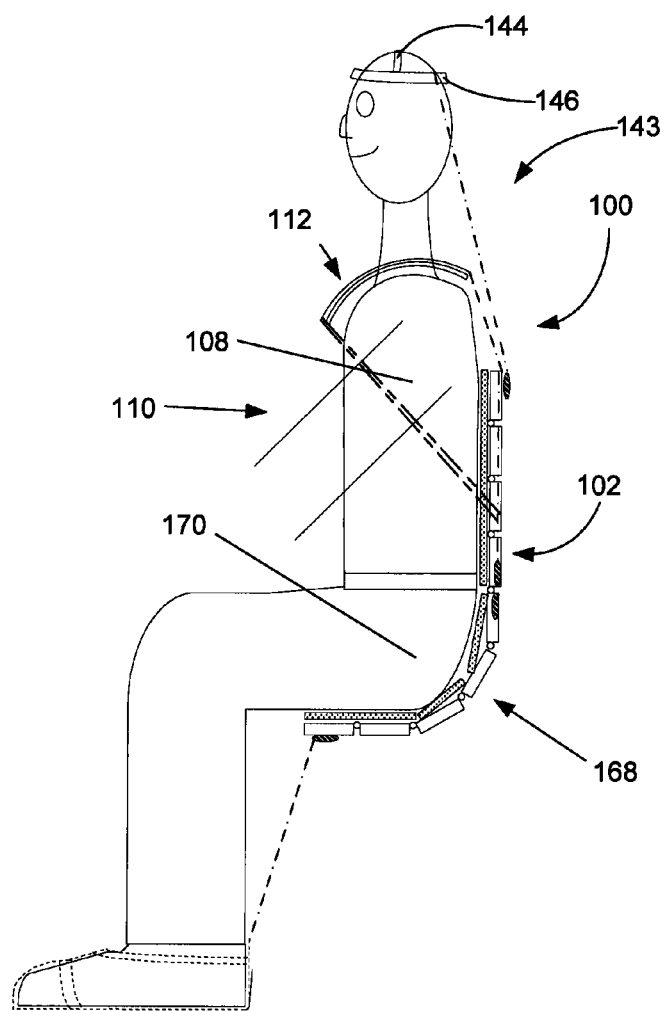
FIG. 7 depicts in side view an exemplary embodiment of the framework includes at least a seat portion.

FIG. 7 reveals in side view an exemplary embodiment of the framework 102 includes at least a seat portion 168 (also referred to herein as a seat structure 168) worn adjacent a buttock 170 of the user 110, the seat portion 168 substantially secures the framework 102 adjacent the body 108 and the buttock 170 while the user 110 sits on the buttock 170 to perform the activity.

When the user 110 performs the activity sitting on the buttock 170, the seat portion 168 is configured to apply tension through the shoulder attachment 112, which helps to substantially secure the framework 102 in a predetermined relative position adjacent the body 108 and the buttock 170, and facilitate the anti-gravity support.

Figure 8:
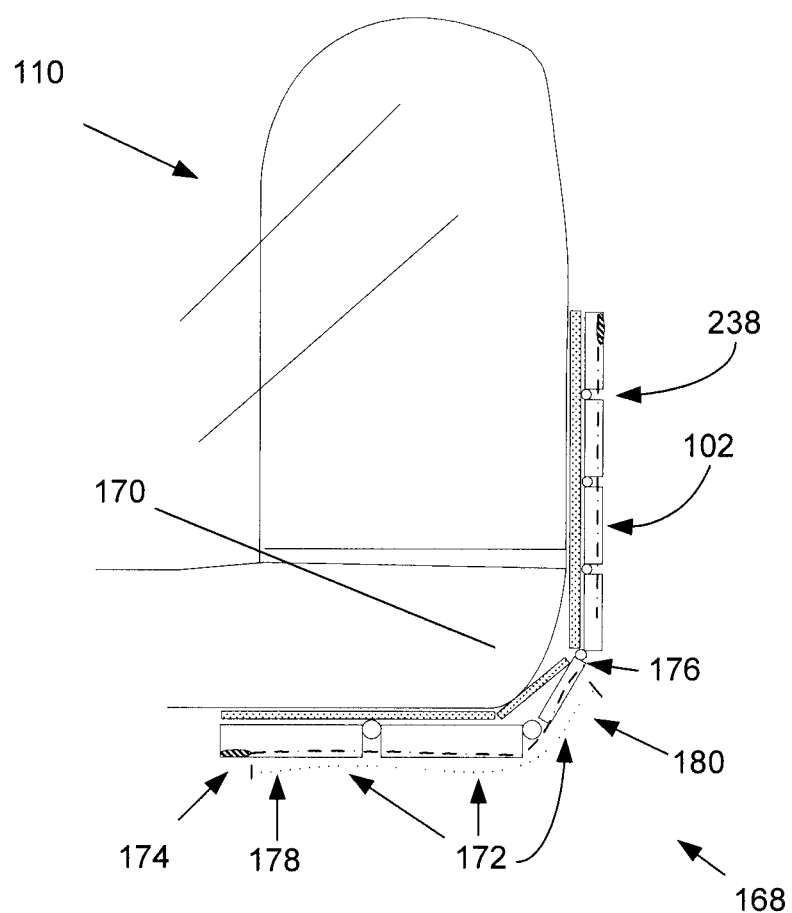
FIG. 8 demonstrates in bottom an exemplary embodiment of an anti-fatigue device includes at least a plurality of seat plates.

FIG. 8 shows in bottom an exemplary embodiment of an anti-fatigue device 100 includes at least wherein the seat portion 168 includes at least a plurality of seat plates 172 movable with respect to each other, a seat hookup member 174 coupled to at least one of the plurality of seat plates 172, and a seat connection member 176 coupled to at least one of the plurality of seat plates 172, the seat hookup member 174 and the seat connection member 176 coupled to each other by a seat cable 178 therebetween, wherein the user 110 configures the seat cable 178 to a predetermined seat cable length 180 so that the plurality of seat plates 172 are substantially immovable with respect to each other in at least a first direction 182 during the anti-gravity support.

Hookup Member and Connection Member.

In exemplary embodiments, the disposition of a hookup member (such as 104, 128, 142, 152, and 174) and a connection member (such as 106, 130, 146, 156, and 176) may be reversed. In other exemplary embodiments, the hookup member and the connection member may be integral to the framework, head support halo, leg support, shoulder portion, etc. In another exemplary embodiment, the hookup member and the connection member may be attached, joined, or otherwise fastened to the framework, head support halo, leg support, shoulder portion, etc. by one or more of a variety of techniques, including but not limited to adhesive, mechanical fastener, etc.

In some embodiments, the hookup member will be coupled to a cable (discussed below) by adhesive, mechanical fastener, structure configured to capture the cable tied down, etc. In other embodiments, the hookup member is characterized as a take-up reel 200. As shown by FIG. 5, in a preferred embodiment the anti-fatigue device 100 includes: a shoulder attachment take-up 201, preferably in the form of take-up reel 200, secured to the framework 112; a head connecting member take-up 203, preferably in the form of take-up reel 200, secured to the framework 112; a leg linking member take-up 205, preferably in the form of take-up reel 200, secured to the framework 112; a backbone attachment take-up 207, preferably in the form of take-up reel 200, secured to the framework 112; and a seat attachment take-up 211, preferably in the form of take-up reel 200, secured to the framework 112.

Figure 9:
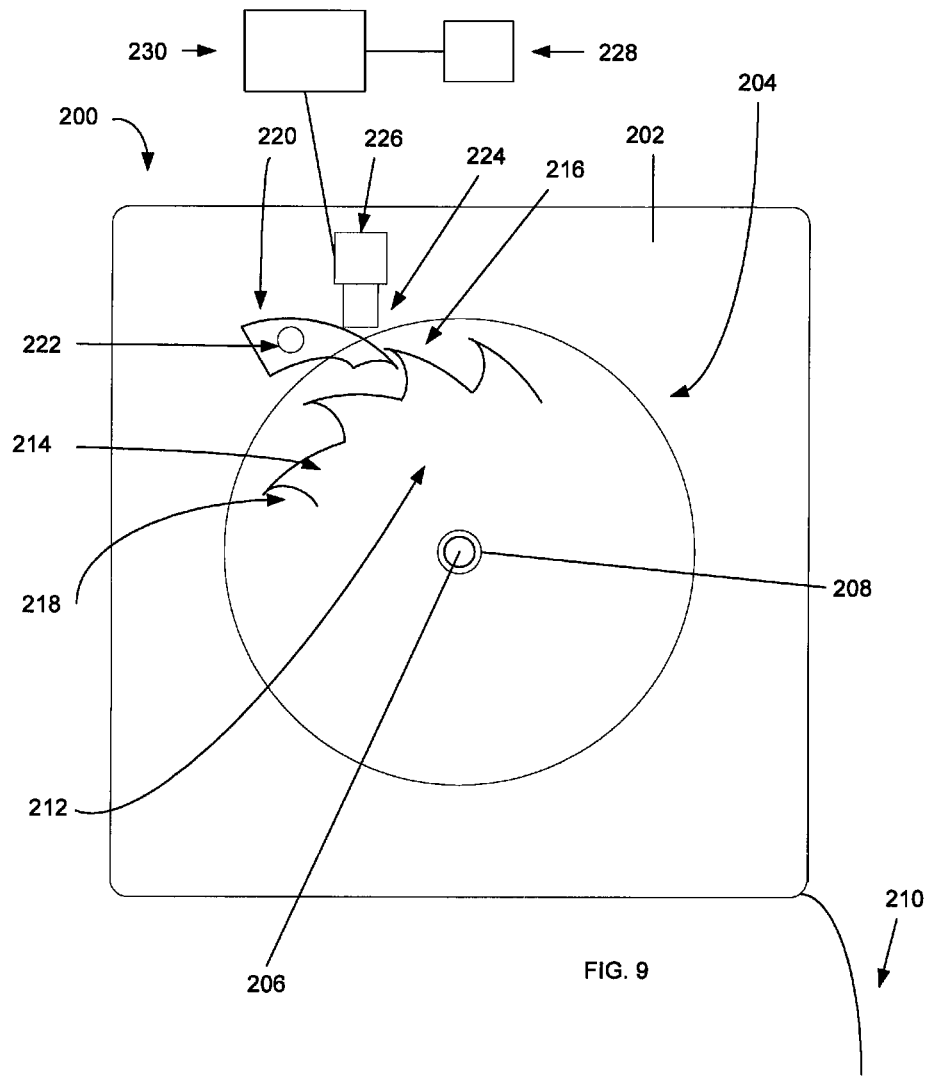
FIG. 9 reveals a partial cutaway view of an embodiment of a take-up reel.

FIG. 9 shows a partial cutaway view of an embodiment of the take-up reel 200 includes at least a housing 202; a spool 204 configured to rotate about an axis 206 of the housing 202; and a retention member 208 biases the spool 204 to collect the cable 210 about the spool 204, the user applies force tension to the cable 210 to overcome the retention member 208 bias so that the cable 210 has payout from the spool 204.

FIG. 9 further illustrates another embodiment of the take-up reel 200 further includes at least a round gear 212 coupled for rotation with the spool 204; a plurality of teeth 214 on the round gear 212, the teeth 214 are configured with a moderate slope on a first edge 216 and a much steeper slope on a second edge 218; a pawl 220 adjacent the housing 202, a biasing member 222 adjacent the pawl 220, the biasing member 222 configured to urge the pawl 220 away from engagement with the teeth 214; a ram 224 housed in ram housing 226 adjacent the pawl 220; a power source 228 for operation of the ram 224; and an activation switch 230 coupled to the ram 224 and power source 228, the ram is biased into the ram housing 226 in a first position that allows the pawl 220 to not engage the teeth 214 to permit rotation of the spool 204, and the ram 224, responsive to the switch activation 230, is urged out of the ram housing 226 in a second position to urge the pawl 220 to engage the teeth 214 to restrict rotation of the spool 204.

In another embodiment, when the teeth 214 move in the unrestricted (e.g., forward) direction, the pawl 220 easily slides up and over the first edge 216 of the teeth 214, with a retention member 208 forcing the pawl 220 (often with an audible 'click') into the depression between the teeth 214 as it passes the tip of each tooth 214. When the teeth 214 move in the opposite (backward) direction, however, the pawl 220 will catch against the second edge 218 of the first tooth 214 it encounters, thereby locking it against the tooth 214 and preventing any further motion in that direction.

In an exemplary embodiment, the power source 228 is a battery, such as lithium ion, or other suitable type, disposed in the anti-fatigue device. In an exemplary embodiment, the power source is disposed in interconnected backbone plates and seat plates. Multiple batteries may be disposed on one or more interconnected backbone plates and seat plates. In exemplary embodiments, batteries may be connected in parallel for higher current and in series for higher voltage, depending on the operation needs of the anti-fatigue device. The various components of the take-up reel 200 are configured to minimize power source use and maximize power source life cycle. In an alternative embodiment the mains may be used at the power source.

The interface controls for the power source 228 may configured in the front portion, interconnected backbone plates, seat plates, or any other suitable location on the anti-fatigue device. The interface controls may operate one take-up reel, all the take-up reels, or any combination of the take-up reels. The interface controls may have consist of one on/off switch, or more elaborate switches, to allow the user to engage and disengaged the anti-fatigue device. Safety mechanisms can be incorporated into the interface controls so the anti-fatigue device does not disengage the anti-fatigue device when there is anti-gravity support tension in the cables.

Cable.

In exemplary embodiments, a cable (such as 112, 132, 148, 158, and 178) can take a variety of forms. The cable must configured for a minimum break strength greater than the anti-gravity support force required while the user 110 performs the activity plus a safety factor, e.g., 400 lbs or greater.

The cable may be manufactured from a variety of materials, including but not limited to polymer (e.g., nylon), metal (e.g. stainless steel, galvanized steel), fishing line, etc. In some embodiments, the cable may be manufactured from elastomeric material, which allows a flexibility to the cable length in the engaged position. Other appropriate materials for constructing a cable will be known to one skilled in the art. Alternatively, a biasing member 232 (which may take a variety of forms, known to one skilled in the art) may be disposed in series with the cable 234, between the plate 236 and the cable 234, to allow the flexibility, as shown in FIG. 10. Other appropriate mechanisms for disposing a biasing member to provide cable flexibility will be known to one skilled in the art.

The cable be substantially a single piece between the hookup member and connection member. In an alternative embodiment, the cable has a plurality of segments joined by any number of fasteners, known to one skilled in the art including but not limited to a cam buckle 238, an example of which is shown in FIG. 11.

FIG. 12 depicts in section view an exemplary embodiment of the cable 234 may be captured in a lumen 240 of a cableway 242. The cableway 242 provides a protective coating to the cable 234 between the hookup member and connection member. The cableway 242 may be manufactured from a variety of materials, including but not limited to nylon, natural fabric, synthetic fabric, silk, etc. Other appropriate materials will be known to one skilled in the art. The cableway 242 may used in the anti-fatigue device wherever a cable 234 is needed.

Head Support Halo and Leg Support.

In exemplary embodiments, the support (such as 144 and 154) may type a variety of forms. In the exemplary embodiments of the anti-fatigue device, the support is configured to securely fit adjacent the user. The support may be manufactured from a variety of materials, including but not limited to polymer, metal, etc. Other appropriate materials will be known to one skilled in the art.

The support may have a padded surface adjacent the user 110 for comfort of the user. The padded surface may be manufactured from foam, or other suitable material known to one skilled in the art.

Backbone Portion, Seat Portion, Shoulder Portion, and Front Portion.

In exemplary embodiments, a plate (126 and 172) and a portion (121, 138, and 168) may take a variety of forms. Analogous to the seat portion 168 formed by the plurality of seat plates 172, the plurality of interconnected backbone plates 126 can be characterized as forming a backbone portion, the shoulder portion 138 can be formed from a plurality of shoulder plates, and the front portion 121 can be formed from a plurality of front plates.

The plate and the portion create a firm foundation, which maintains help relative positions of the framework, cables, etc, during anti-gravity support for the user performing the activity. In addition, the plates and the portion distribute the forces experienced by the user when performing the activity under anti-gravity support for user comfort.

The plate and portion may be manufactured from a variety of materials, including but not limited to polymer, metal, wood, etc. Other appropriate materials will be known to one skilled in the art.

In an exemplary embodiment, the portion may be manufactured as one plate, as one plate with material selectively configured (e.g., removed) to create flexibility, or a plurality of plates joined by appropriate fasteners. Such fasteners may include, but are not limited to, a rotatable fastener (such as 238 of FIG. 7). The fastener may be manufactured of any suitable material known to the skilled artisan, such as metal, polymer, etc. When a plurality of plates are used, a plurality of fasteners are useful to restrict a lateral rotation during use by the user.

Figure 13:
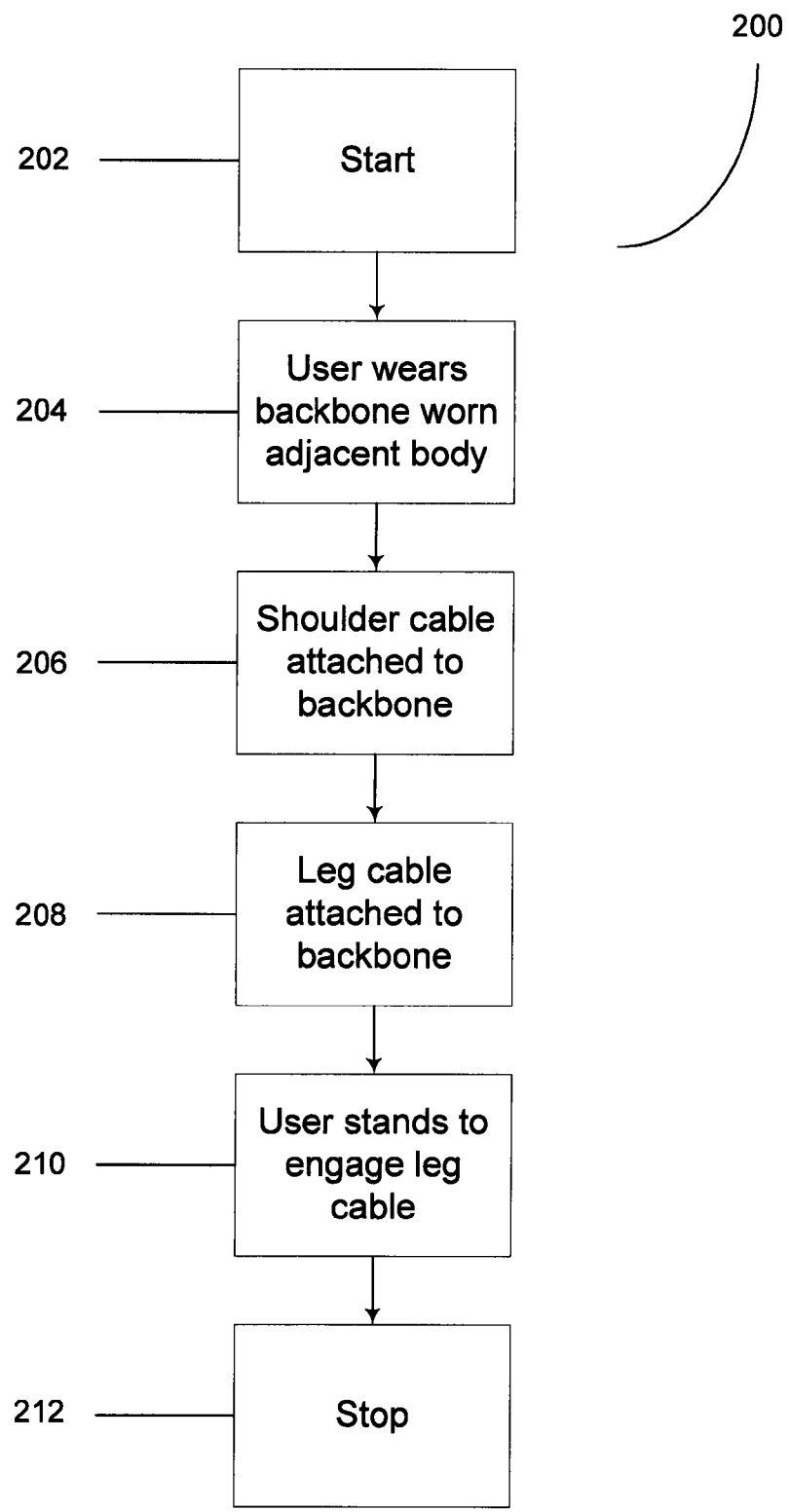
FIG. 13 shows a flowchart of exemplary method steps.
Figure 14:
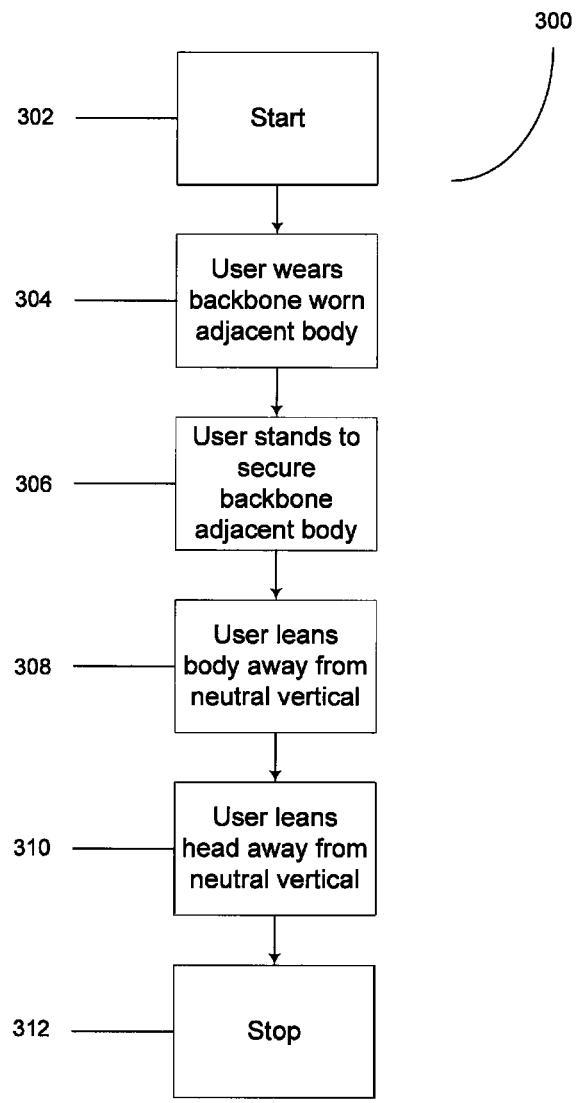
FIG. 14 shows a flowchart of exemplary method steps.

The FIGS. 13 and 14 disclose exemplary embodiments of methods for the inventive anti-fatigue device. The flowchart 200 of FIG. 13 shows exemplary method steps of a process of providing an anti-gravity support of a body of a user that reduces user fatigue from an activity the user performs. The process commences at start process step 202 and continues at process step 204. At process step 204, a furnished backbone portion is worn adjacent the body of the user. At process step 206, a shoulder cable is attached to the backbone portion. At process step 208, a leg cable is attached between the backbone portion and a leg of the user, wherein the leg cable is configured to substantially secure the backbone portion adjacent the body while the user stands on the leg. At process step 210, the user stands on the leg to engage the shoulder cable to provide an anti-gravity support of the body of the user that reduces user fatigue from the activity the user performs, and the process concludes at end process step 212. The process steps 204, 206, and 208 may be performed in any order in relation to each other.

The flowchart 300 of FIG. 14 shows exemplary method steps of a process of providing an anti-gravity support of a body of a user that reduces user fatigue from an activity the user performs. The process commences at start process step 302 and continues at process step 304. At process step 304, a furnished backbone portion is worn adjacent the body of the user. The backbone portion communicates with at least a shoulder cable, a leg cable, and a head cable. The body is captured by the shoulder cable adjacent the backbone portion. The leg cable is coupled to a leg of the user. The head cable is coupled to a head of the user. At process step 306, the user stands on the leg to substantially secure the backbone portion adjacent the body. At process step 308, the user leans the body away from a neutral vertical position to engage the shoulder cable to provide anti-gravity support of the body of the user that reduces user fatigue from the activity the user performs. At process step 310, the user leans the head away from the neutral vertical position to provide to provide an anti-gravity support of the head of the user that reduces user fatigue from the activity the user performs, and the process concludes at end process step 312. The process step 310 may be performed before process step 308.

In another exemplary embodiment, a seat portion is furnished rather than a leg cable. Engaging the seat portion substantially secures the framework adjacent the body.

In an exemplary embodiment, engaging the head cable to provide an anti-gravity support of the body of the user that reduces user fatigue from the activity the user performs occurs without engaging the shoulder cable. In an alternative exemplary embodiment, engaging the shoulder cable to provide an anti-gravity support of the body of the user that reduces user fatigue from the activity the user performs occurs without engaging the head cable.

The present invention has been described as providing anti-gravity support when the user leans forward, however alternative embodiments, such as configuring the anti-fatigue device to provide anti-gravity support when the user leans backwards, e.g., while working on a ceiling, are possible.

While the invention has been described in connection with an exemplary embodiment, it is not intended to limit the scope of the invention to the particular form set forth, but on the contrary, it is intended to cover such alternatives, modifications, and equivalents as may be included within the spirit and scope of the invention as defined by the appended claims.

It will be clear that the present invention is well adapted to attain the ends and advantages mentioned as well as those inherent therein. While presently preferred embodiments have been described for purposes of this disclosure, numerous changes may be made which will readily suggest themselves to those skilled in the art and which are encompassed by the appended claims.

What is claimed is:

1. An anti-fatigue device comprising:
   a plurality of interconnected backbone plates;
   a shield adjacent the plurality of interconnected backbone plates; and
   a plurality of seat plates interacting with the plurality of interconnected backbone plates, wherein the interconnected back plates, the shield, and the plurality of seat plates cooperatively form a framework;
   a shoulder hookup member secured to the framework;
   a shoulder connection member attached to the framework; and
   a shoulder attachment coupled between the shoulder hookup member and the shoulder connection member.

2. The device of claim 1, in which the shoulder attachment includes a first end coupled to the shoulder hookup member, a second end coupled to the shoulder connection member, and a medial portion disposed between said first and second ends, wherein an interaction of the shoulder and the framework provides an anti-gravity support.

3. The device of claim 2, further comprising a head support structure connected to the framework.

4. The device of claim 3, further comprising a head hookup member secured to the framework and interconnecting the head support structure with the framework.

5. The device of claim 4, further comprising a leg support linked to the framework.

6. The device of claim 5, further comprising a linking member interlinking the leg support and the framework.

7. The device of claim 1, further comprising:
   a backbone attachment interconnecting each of the plurality of interconnected backbone plates, said backbone attachment providing a first end secured to the framework; and a backbone attachment take-up secured to said framework, wherein said backbone attachment take-up interacts with a second end of the backbone attachment to control a spacing between each of the plurality of interconnected backbone plates.

8. The device of claim 1, further comprising:
   a shoulder attachment take-up secured to said framework, wherein said shoulder attachment take-up interacts with a first end of the shoulder attachment to position the plurality of interconnected backbone plates, and further wherein the shoulder attachment is coupled to the framework by a second end of the shoulder attachment.

9. The device of claim 1, further comprising:
   a head connecting member take-up secured to said framework, wherein said head connecting member take-up interacts with a first end of a connecting member, and further comprising a head support structure secured to a second end of the connecting member.

10. The device of claim 1, further comprising:
    a leg linking member take-up secured to said framework, wherein said leg linking member take-up interacts with a first end of a linking member to position the plurality of interconnected backbone plates, and further wherein the linking member is coupled to the framework by a second end of the linking member.

11. A method of forming an anti-fatigue device, by steps comprising:
    providing a plurality of interconnected backbone plates;
    attaching a shield to the plurality of interconnected backbone plates; and
    interconnecting a plurality of seat plates with the plurality of interconnected backbone plates, wherein the interconnected back plates, the shield, and the plurality of seat plates cooperatively form a framework of the anti-fatigue device;
    securing a shoulder hookup member to the framework;
    attaching a shoulder connection member to the framework; and
    coupling a shoulder attachment between the shoulder hookup member and the shoulder connection member.

12. The method of claim 11, by steps further comprising:
    fastening a leg linking member take-up to said framework, wherein said leg linking member take-up interacts with a first end of a linking member to position the plurality of interconnected backbone plates, and further wherein the linking member is coupled to the framework by a second end of the linking member.

13. The method of claim 11, by steps further comprising: linking a second take-up to said framework, wherein said second take-up interacts with a head support structure to position the plurality of interconnected backbone plates.

14. The method of claim 11, by steps further comprising: interconnecting a backbone attachment to each of the plurality of interconnected backbone plates, said backbone attachment providing a first end secured to the framework; and attaching a backbone attachment take-up to said framework, wherein said backbone attachment take-up interacts with a second end of the backbone attachment to control a spacing between each of the plurality of interconnected backbone plates.

15. The method of claim 11, by steps further comprising: securing a shoulder attachment take-up to said framework, wherein said shoulder attachment take-up interacts with a first end of the shoulder attachment to position the plurality of interconnected backbone plates, and further wherein the shoulder attachment is coupled to the framework by a second end of the shoulder attachment.

16. The method of claim 11, by steps further comprising: attaching a head connecting member take-up to said framework, wherein said head connecting member take-up interacts with a first end of a connecting member, and further comprising a head support structure secured to a second end of the connecting member.

* * * * *